US011161299B2

(12) United States Patent
Wen et al.

(10) Patent No.: US 11,161,299 B2
(45) Date of Patent: Nov. 2, 2021

(54) BIOPRINTER SPRAY HEAD ASSEMBLY AND BIOPRINTER

(71) Applicant: REVOTEK CO., LTD, Sichuan (CN)

(72) Inventors: Xuemin Wen, Chengdu (CN); Yijun Li, Chengdu (CN); Deming Wang, Chengdu (CN)

(73) Assignee: Revotek Co., Ltd, Sichuan (CN)

(*) Notice: Subject to any disclaimer, the term of this patent is extended or adjusted under 35 U.S.C. 154(b) by 116 days.

(21) Appl. No.: 16/067,541

(22) PCT Filed: Dec. 30, 2015

(86) PCT No.: PCT/CN2015/099822
§ 371 (c)(1),
(2) Date: Jun. 29, 2018

(87) PCT Pub. No.: WO2017/113167
PCT Pub. Date: Jul. 6, 2017

(65) Prior Publication Data
US 2019/0255770 A1 Aug. 22, 2019

(51) Int. Cl.
*B29C 64/209* (2017.01)
*B29C 64/393* (2017.01)
(Continued)

(52) U.S. Cl.
CPC .............. *B29C 64/209* (2017.08); *A61F 2/02* (2013.01); *A61M 35/00* (2013.01); *B05B 7/061* (2013.01);
(Continued)

(58) Field of Classification Search
CPC ........... B05B 7/061; B05B 7/16; B05B 13/04; B05B 15/50; B05B 12/124; B29C 64/209; B29C 64/112; B29C 64/106; B29C 64/393
See application file for complete search history.

(56) References Cited

U.S. PATENT DOCUMENTS

2012/0322154 A1 12/2012 Park et al.

FOREIGN PATENT DOCUMENTS

CN 2 764 486 Y 3/2006
CN 2764486 Y * 3/2006
(Continued)

OTHER PUBLICATIONS

International Search Report and Written Opinion for PCT/CN2015/099822, dated Sep. 21, 2016.
(Continued)

*Primary Examiner* — Joseph S Del Sole
*Assistant Examiner* — Mohamed K Ahmed Ali
(74) *Attorney, Agent, or Firm* — Wolf, Greenfield & Sacks, P.C.

(57) ABSTRACT

The present disclosure relates to a bioprinter spray head assembly and a bioprinter, wherein the bioprinter spray head assembly comprises an outer nozzle having a second channel and an inner nozzle having a first channel, the inner nozzle is coaxially provided within the second channel, the first channel forms a first material channel, and an annular space between the outer nozzle and the inner nozzle forms a second material channel, which surrounds the first material channel at an outlet of the first material channel, for converging a second material sprayed from an outlet of the second material channel toward a first material sprayed from the outlet of the first material channel, so as to form a fluid printing unit. Such spray head assembly can allow that the second material uniformly wraps the first material at the outlet of the spray head assembly, so as to form a fluid printing unit having a high quality to protect the cells, thereby reducing the cell damage caused by the extrusion pressure and the frictional force subjected in the printing process, so as to improve the survival rate of the cells.

9 Claims, 3 Drawing Sheets

(51) Int. Cl.

| | |
|---|---|
| ***B29C 64/112*** | (2017.01) |
| ***B29C 64/106*** | (2017.01) |
| ***B33Y 30/00*** | (2015.01) |
| ***A61F 2/02*** | (2006.01) |
| ***A61M 35/00*** | (2006.01) |
| ***C12M 3/00*** | (2006.01) |
| ***B05B 7/06*** | (2006.01) |
| ***B05B 7/16*** | (2006.01) |
| ***B05B 12/12*** | (2006.01) |
| *B05B 13/04* | (2006.01) |
| *B05B 15/50* | (2018.01) |

(52) U.S. Cl.

CPC .............. *B05B 7/16* (2013.01); *B05B 12/124* (2013.01); *B29C 64/106* (2017.08); *B29C 64/112* (2017.08); *B29C 64/393* (2017.08); *B33Y 30/00* (2014.12); *C12M 21/08* (2013.01); *B05B 13/04* (2013.01); *B05B 15/50* (2018.02)

(56) References Cited

FOREIGN PATENT DOCUMENTS

| | | | |
|---|---|---|---|
| CN | 103911678 | A | 7/2014 |
| CN | 104441654 | | 3/2015 |
| CN | 104873300 | A | 9/2015 |
| CN | 204722376 | | 10/2015 |
| CN | 105167879 | A | 12/2015 |
| CN | 204839829 | | 12/2015 |

OTHER PUBLICATIONS

Japanese Office Action dated Oct. 8, 2019 in connection with JP Patent Application No. JP2018-534155.

Gao et al., Coaxial nozzle-assisted 3D bioprinting with built-in microchannels for nutrients delivery. Biomaterials. Aug. 2015;61:203-15. doi: 10.1016/j.biomaterials.2015.05.031. Epub May 19, 2015.

Extended European Search Report and Search Opinion dated Aug. 14, 2019, in connection with EP Application No. 15911796.9.

International Report on Patentability for Application No. PCT/CN2015/099822, dated Jul. 12, 2018.

PCT/CN2015/099822, Jul. 12, 2018, International Preliminary Report on Patentability and English translation thereof.

* cited by examiner

BIOPRINTER SPRAY HEAD ASSEMBLY AND BIOPRINTER

RELATED APPLICATIONS

This application is a national stage filing under 35 U.S.C. § 371 of International Patent Application Serial No. PCT/CN2015/099822, filed Dec. 30, 2015, the content of which is incorporated herein by reference in its entirety.

FIELD OF THE DISCLOSURE

The present disclosure relates to the field of bioprinting, and especially relates to a bioprinter spray head assembly and a bioprinter.

BACKGROUND OF THE DISCLOSURE

3D Biological printing refers to the printing of biological materials (including natural materials and synthetic materials or cellular solutions) into a designed three-dimensional structure through the principles and methods of 3D printing, which is different from 3D printing technology. The biological tissues or organs produced by 3D biological printing technology also have certain biological functions and need to provide conditions for the further growth of cells and tissues. Exactly due to the aforementioned characteristics, the 3D biological printing technology is confronted with many specific technical problems in development.

Among them, in the field of 3D biological printing, the technique of taking cells as a printing material is referred to as cell three-dimensional printing technology. People may utilize cells and biocompatible materials to make bio-ink. The nozzle moves and sprays the bio-ink, and the movement of the spray head is controlled by a program to print the bio-ink. The bio-ink is printed and molded according to a three-dimensionally constructed digital model of a preset target print object.

The spray head for bioprinting in the prior art is similar to a nozzle of a syringe needle, which is mounted directly on the bioprinter. The spray head device of such bioprinter has a simple structure, is mainly used to fill active cells into a stent material, but cannot be wrapped before printing. Furthermore, in the process of directly spraying cells to the printing platform using a spray head, the extrusion pressure and the frictional force of the sidewalls of the nozzle over the cells may cause the cells in the bio-ink to be greatly damaged, so that an adverse effect may be produced over the survival rate of the cells, to further affect the construction of a biological construct.

SUMMARY OF THE DISCLOSURE

In order to overcome the above technical defects, the technical problem solved by the present disclosure is to provide a bioprinter spray head assembly and a bioprinter capable of printing a plurality of printing materials at the same time. Further, a plurality of printing materials may also be combined together before printing. Preferably, the first material as the bio-ink is preferably wrapped using the second material, so that it also has the advantage of protecting the cells in the sprayed bio-ink from damage as much as possible.

In order to solve the aforementioned technical problems, the first aspect of the present disclosure provides a bioprinter spray head assembly, comprising an outer nozzle provided with a second channel and an inner nozzle provided with a first channel, wherein the inner nozzle is coaxially provided within the second channel, the first channel forms a first material channel and an annular space between the outer nozzle and the inner nozzle forms a second material channel, which surrounds the first material channel at an outlet of the first material channel, for converging a second material sprayed from an outlet of the second material channel toward a first material sprayed from the outlet of the first material channel, so as to form a fluid printing unit of a biological printing material.

In the basic technical solution, the second flow channel can guide and gradually converge the second material toward the first material, so as to converge the second material and the first material together. For example, the second material at the outlet of the spray head assembly can uniformly wrap the first material at the outlet of the spray head assembly, so as to form a fluid printing unit having a high quality to protect the cells, thereby reducing the cell damage caused by the extrusion pressure and the frictional force subjected in the printing process, so as to improve the survival rate of the cells.

Further, the bioprinter spray head assembly further comprises a first material supply pipe and an outer nozzle fixing portion, wherein the outer nozzle is detachably connected to the outer nozzle fixing portion, and the inner nozzle is detachably connected to the first material supply pipe.

In the improved technical solution, the outer nozzle and the inner nozzle are designed into a detachable and individually replaceable structure. When need to replace, it is convenient to remove the nozzle portion of the spray head assembly adjacent to the outlet, which only involves the removal of local parts, so that the replacement is very efficient.

Further, the bioprinter spray head assembly comprises a nozzle kit group consisting of a plurality of nozzles of different specifications, wherein the outer nozzle and the inner nozzle are selected from the nozzle kit group.

In the improved technical solution, by replacing the inner nozzle and the outer nozzle of different specifications, the spray head assembly can spray particles of different sizes and wrapping layers of different thicknesses to achieve wrapping controllably.

Further, at the outlet of the second material channel, the outlet of the outer nozzle is lower than the outlet of the inner nozzle.

In the improved technical solution, the extension portion of the outer nozzle can be further tapered along a direction toward the outlet of the first material channel, so as to guide the second material to further converge towards a direction of the first material, to facilitate more reliably and adequately wrapping the first material.

Further, the outer nozzle comprises a first guide portion, and the inner nozzle comprises a second guide portion, wherein the first guide portion and the second guide portion are provided adjacent to an outlet of the spray head, and a first annular space between the first guide portion and the second guide portion is tapered along a direction toward the outlet of the first material channel.

In the improved technical solution, the second material channel which is tapered adjacent to the outlet along a direction toward the outlet of the first material channel, can guide the second material to further converge to the first material in the spraying process, so that the first material is wrapped at the outlet of the first material channel, thereby avoiding from being damaged due to the effect of the mechanical frictional force when the first material sprayed.

Further, the outer nozzle further comprises a first body portion connected with the first guide portion, and the inner nozzle further comprises a second body portion connected with the second guide portion, wherein a second annular space between the first body portion and the second body portion is at least partially tapered towards a direction of the outlet of the second material channel.

In the improved technical solution, the annular space between the first body portion and the second body portion is designed in an at least partially tapered structure, which may further increase the pressure of the second material to increase the flow velocity, so that the second material which flows more smoothly within the second material channel, is less likely to be clogged, and wraps the first material more adequately and uniformly at the outlet of the first material channel.

Further, a portion of the first material channel in the first annular space is elongated, and a portion of the first material channel in the second annular space is at least partially tapered towards a direction of the outlet of the first material channel.

In the improved technical solution, the first material channel adjacent to the outlet is designed to be an elongated channel, which can guide the first material to be sprayed more smoothly to be wrapped by the second material.

In order to solve the aforementioned technical problem, the present disclosure provides a second aspect, which provides a bioprinter, comprising the bioprinter spray head assembly according to the aforementioned embodiments.

In the basic technical solution, the bioprinter can make the produced various biological constructs maintain a high activity and a long service life by obtaining a high-quality biological printing material.

Further, the bioprinter further comprises a pressure adjustment device for controlling respective fluid pressures within the first material channel and the second material channel.

In the improved technical solution, by providing a pressure adjustment device, the first material and the second material can be controlled to be sprayed from the outlet at different speeds.

Further, the bioprinter further comprises a temperature control device for controlling respective temperatures of the first material channel and the second material channel.

In the improved technical solution, by providing a temperature control device, it is beneficial to keep the activity of the biological material in the printing process, and especially when a biological printing material having a high viscosity is used, it can improve the fluidity and avoid the phenomenon of the clogging of the nozzle due to a low temperature as much as possible, so as to raise the printing efficiency.

Further, the bioprinter further comprises a position detecting device for judging an initial printing position of the spray head assembly.

In the improved technical solution, by providing a position detecting device, the height of the printing platform can be judged before printing to determine an initial printing position of the spray head assembly, thereby printing more accurately.

Accordingly, based on the aforementioned technical solution, the bioprinter spray head assembly of the present disclosure uses such a structural form that the inner and outer nozzles are coaxially designed in two layers. The first channel of the inner nozzle forms a first material channel, and the annular space between the outer nozzle and the inner nozzle forms a second material channel, enabling the second material sprayed from the outlet of the second material channel to wrap the first material sprayed from the outlet of the first material channel to form the fluid printing units of a biological printing material to protect the cells, thereby reducing the cell damage caused by an extrusion pressure and a frictional force subjected in the printing process, so as to improve the survival rate of the cells and present a high reliability. Moreover, the second material channel coaxially surrounds the first material channel adjacent to the outlet of the first material channel, which is favorable for more uniformly wrapping the second material outside the first material, and avoiding a phenomenon of uneven thickness as much as possible, so as to form a fluid printing unit with high quality.

BRIEF DESCRIPTION OF THE ACCOMPANYING DRAWINGS

The drawings described herein are used to provide a further understanding of the present disclosure and constitute a part of the present application. The illustrative embodiments of the present disclosure as well as the descriptions thereof, which are merely used for explaining the present disclosure, do not constitute improper definitions on the present disclosure. In the drawings.

DETAILED DESCRIPTION OF THE PREFERRED EMBODIMENTS

Figure 1:
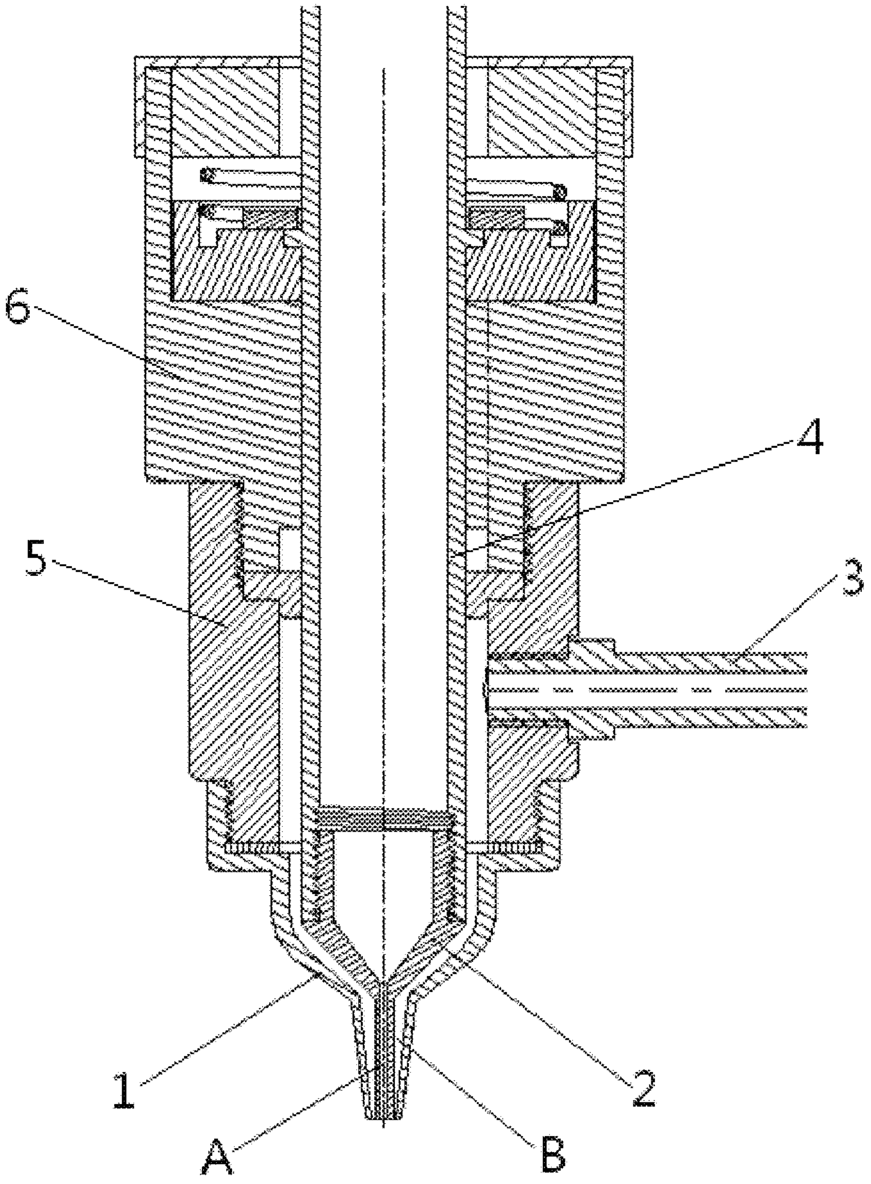
FIG. 1 is a schematic view of the structure of one embodiment of the bioprinter spray head assembly of the present disclosure.

Next, the technical solution of the present disclosure is further described in detail by means of the drawings and embodiments.

The specific embodiments of the present disclosure are further described in order to facilitate understanding of the concept of the present disclosure, the technical problem to be solved, the technical features constituting the technical solution and the technical effect produced therefrom. It is necessary to explain that, the explanations for such embodiments do not constitute definitions on the present disclosure. In addition, the technical features involved in the embodiments of the present disclosure described below may be combined with each other as long as they do not constitute a conflict there between.

The spray head assembly of the bioprinter in the prior art cannot wrap the cells before printing, which may result in cellular damage in the printing process. Therefore, the present disclosure provides a bioprinter spray head assembly, and its structure may refer to the schematic views shown in FIGS. 1 and 2. In one illustrative embodiment, there comprise an outer nozzle 1 provided with a second channel C and an inner nozzle 2 provided with a first channel, wherein the inner nozzle 2 is coaxially provided within the second channel C, the first channel forms a first material channel A, and an annular space between the outer nozzle 1 and the inner nozzle 2 forms a second material channel B, which surrounds the first material channel A adjacent to an outlet of the first material channel A, for converging a second material sprayed from an outlet of the second material channel B toward a first material sprayed from the outlet of the first material channel A, so as to form a fluid printing unit of a biological printing material.

The first material channel A and the second material channel B which may be used to convey the same kind of material, but also to convey different kinds of materials, may be used at the same time and may also be used independent from each other. The first material and the second material may be the same, and may also be different.

When the first material and the second material are different, the first material may be a main material, for example a dispersed phase solution (homogeneous continuous fluid) or a suspension containing cells (non-homogeneous fluid), and the second material may be an auxiliary material, for example, a surrounding sheath fluid or a nutrient solution. The fluid printing unit is a printing unit composed of a biological printing material. For example, it may be formed by wrapping a main material with an auxiliary material.

The bioprinter spray head assembly of the present disclosure uses such a structural form that the inner and outer nozzles are coaxially arranged in two layers. The first channel of the inner nozzle forms a first material channel, and the annular space between the outer nozzle and the inner nozzle forms a second material channel, enabling the auxiliary material sprayed from the outlet of the second material channel to wrap the main material sprayed from the outlet of the first material channel to form a fluid printing unit of a biological printing material to protect the cells, thereby reducing the cell damage caused by an extrusion pressure and a frictional force subjected in the printing process, so as to improve the survival rate of the cells and present a high reliability. Moreover, the form that the second material channel coaxially surrounds the first material channel adjacent to the outlet of the first material channel, it's benefit for more uniformly wrapping the auxiliary material outside the main material, and avoiding a phenomenon of uneven thickness as much as possible, so as to form a fluid printing unit with high quality.

Since the printer needs to regularly clean the inside of the spray head assembly during use, in one improved embodiment, the outer nozzle 1 and the inner nozzle 2 may be made to be a detachable and individually replaceable structure. In this way, when need to replace, it is convenient to remove the nozzle portion of the spray head assembly adjacent to the outlet, which only involves the removal of local parts, so that the replacement is efficient.

In order to achieve such object, a specific structure as shown in FIG. 1 may be used. The bioprinter spray head assembly comprises: a first material supply pipe 4 and an outer nozzle fixing portion 5, wherein the outer nozzle 1 is detachably connected to the outer nozzle fixing portion 5, and the inner nozzle 2 is detachably connected to the first material supply pipe 4. Since there is an annular space present between the first material supply pipe 4 and the outer nozzle fixing portion 5, in order to effectuate relative fixation of the first material supply pipe 4 and the outer nozzle fixing portion 5, a connecting part 6 may be provided at the upper end of the outer nozzle fixing portion 5. The connecting part 6 is mated with the first material supply pipe 4.

Optionally, the outer nozzle 1 and the inner nozzle 2 are respectively threaded connected with the outer nozzle fixing portion 5 and the first material supply pipe 4, and the installation and removal may be realized by rotating the two nozzles. Such connection manner is very reliable and there is no need to add other additional parts for auxiliary connection. In addition to the threaded connection, those skilled in the art may also use a quick-insertion mechanism to achieve a detachable connection. It is only necessary to press or release a locking member to realize the installation and removal of the nozzle.

In order to enable the spray head assembly to spray different specifications of particles and different thicknesses of wrapping fluid, on the basis of the embodiment of a detachable nozzle, there comprises a nozzle kit group, which consists of a plurality of outer nozzles 1 and inner nozzles 2 of different specifications. When a printing mission is performed, it is possible to select appropriate outer nozzles 1 and inner nozzles 2 from the nozzle kit group. Different specifications mean different shapes, dimensions or tapers of the nozzles, but the dimensions at the threaded connection are the same. In this way, different specifications of nozzles may be replaced at any time as necessary, to obtain mating of different apertures and tapers, so as to provide different dimensions of fluid printing units, or acquire a better wrapping effect. Thus, controllable wrapping the main material by the auxiliary material can be realized by replacing different specifications of outer nozzles 1 and inner nozzles 2.

For the aforementioned embodiments, the main material and the auxiliary material may be wrapped at the outlet of the spray head assembly. Generally, at the outlet of the second material channel B, the outlet of the outer nozzle 1 is flush with the outlet of the inner nozzle 2. More preferably, at the outlet of the second material channel 2B, the outlet of the outer nozzle 1 is lower than the outlet of the inner nozzle 2, so that the extension portion can be further tapered along a direction toward the outlet of the first material channel A, so as to guide the auxiliary material to further converge towards a direction of the first material, to facilitate more reliably and adequately wrapping the main material.

In a preferred structural form, the first material channel A is an elongate channel adjacent to the outlet of the spray head assembly, enabling the main material when sprayed to be orientedly guided and sequenced, and reducing the likelihood of clogging. The portion of the second material channel B adjacent to the outlet is tapered along a direction toward the outlet of the first material channel A, which enables applying a pressure to the auxiliary material along the direction toward a direction in which the main material flows, to guide the auxiliary material to be sprayed toward the main material, so as to better wrap the main material; and can also increase the pressure on the auxiliary material to increase the flow velocity, so that the auxiliary material flows out more smoothly to achieve the wrapping. Those skilled in the art may design a tapered degree of the second material channel to achieve wrapping controllably before printing.

Figure 2:
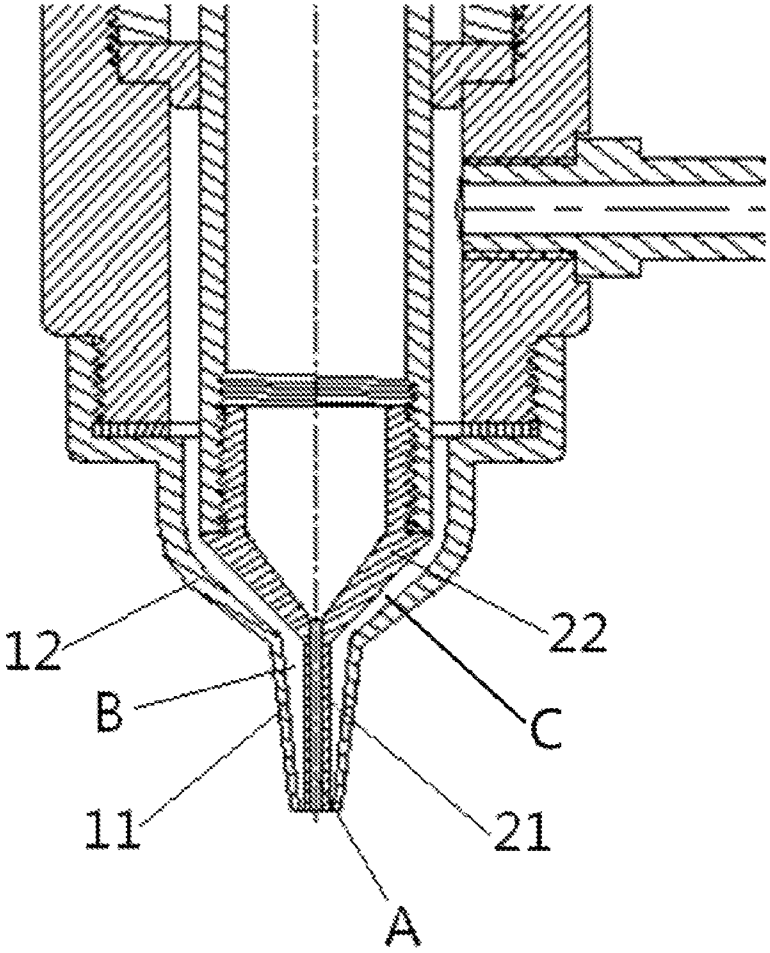
FIG. 2 is an enlarged view of a nozzle portion of the bioprinter spray head assembly shown in FIG. 1.

A specific implementation structure is given below for the embodiment that the second material channel B is tapered. As shown in FIG. 2, the outer nozzle 1 includes a first guide portion 11 and a first body portion 12. The inner nozzle 2 includes a second guide portion 21 and a second body portion 22. The first guide portion 11 and the second guide portion 22 are provided adjacent to the outlet of the spray head assembly, and the annular space between the first guide portion 11 and the second guide portion 21 is tapered along a direction toward the outlet of the first material channel A.

More preferably, the cross-section of the portion of the second material channel B adjacent to the outlet is tapered. The conically tapered form presents a better guiding effect over the fluid than in other shapes, and may also enable that the auxiliary material has the same flow velocity at the same height, and enable that the flow velocities arriving at the outlet of the second material channel are substantially the same, to further effectuate that the auxiliary material uniformly wraps the main material. For example, in the embodiment shown in FIG. 1, the second guide portion 21 is cylindrical, and the first guide portion 11 is in an inverted conical shape. In other embodiments, both the first guide portion 11 and the second guide portion 21 may also be designed in an inverted conical shape, and the first guide portion 11 has a taper that is greater than that of the second guide portion 21.

In the specific structural form, the first body portion 12 includes a first cylindrical portion and a first conical portion. The first conical portion is connected between the first guide portion 11 and the first cylindrical portion. The first cylindrical portion is connected with the outer nozzle fixing portion 5 by threaded fit or in other fastening manners. The outer nozzle fixing portion 5 is provided with a connection tube 3 for leading the auxiliary material into the second material channel B. The second body portion 22 includes a second cylindrical portion and a second conical portion. The second conical portion is connected between the second guide portion 21 and the second cylindrical portion. The second cylindrical portion is connected with the first material supply pipe 4 by threaded fit or in other fastening manners. Wherein, the second conical portion produces a transitional effect, to reduce the cross-sectional area of the first material channel A, so that the main material when flowing out is converted into a fluid printing unit that meets the printing requirements. The first conical portion is designated to be adapted to the second conical portion so as to produce a guiding effect over the auxiliary material. As a better design form, the space of the second material channel B between the first conical portion and the second conical portion is tapered, which may further increase the pressure of the auxiliary material to increase the flow velocity, so that the auxiliary material which flows more smoothly within the second material channel B, is less likely to be clogged, and wraps the main material more adequately at the outlet.

Figure 3:
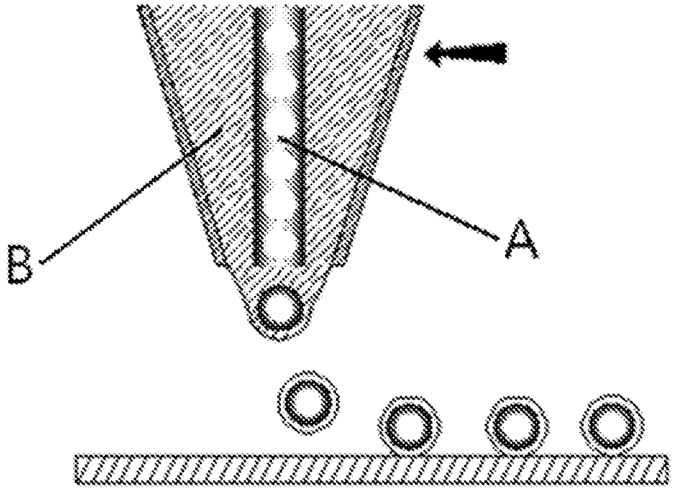
FIG. 3 is a schematic view of a state of the fluid printing unit flowing out in the bioprinter spray head assembly.

For the first material channel A, the first material channel A corresponding to the second guide portion 21 is an elongated channel, and the first material channel A corresponding to the first body portion 12 is tapered at least partially toward the direction of the outlet of the first material channel A, so as to achieve the transition to the elongated channel. In the structure as shown in FIGS. 2 and 3, the first material channel A corresponding to the second cylindrical portion is a cylindrical channel with a large cross-sectional area, and by the transitional effect of the second conical portion, it is realized that the first material channel A corresponding to the second guide portion 21 is an elongated cylindrical channel. Moreover, it is best that the elongated channel is available for channel of a single row of main materials (for example, cells), to guide the main material to be more smoothly sprayed such as to be wrapped by the auxiliary material, thereby forming a biological printing material that meets the dimension requirements.

The operational principles of such spray head assembly according to the present disclosure will be described in detail below in combination with the embodiment shown in FIG. 2. Under the control of the pressure, the main material flows along the first material channel A, and the auxiliary material flows along the tapered second material channel B, and has certain pressure to be attached to the main material arriving at the outlet of the first material channel A when the auxiliary material arrives at the outlet of the second material channel B, to gradually effectuate that it is fully wrapped to form a fluid printing unit, and sequentially sprayed from the outlet of the spray head assembly.

Figure 4:
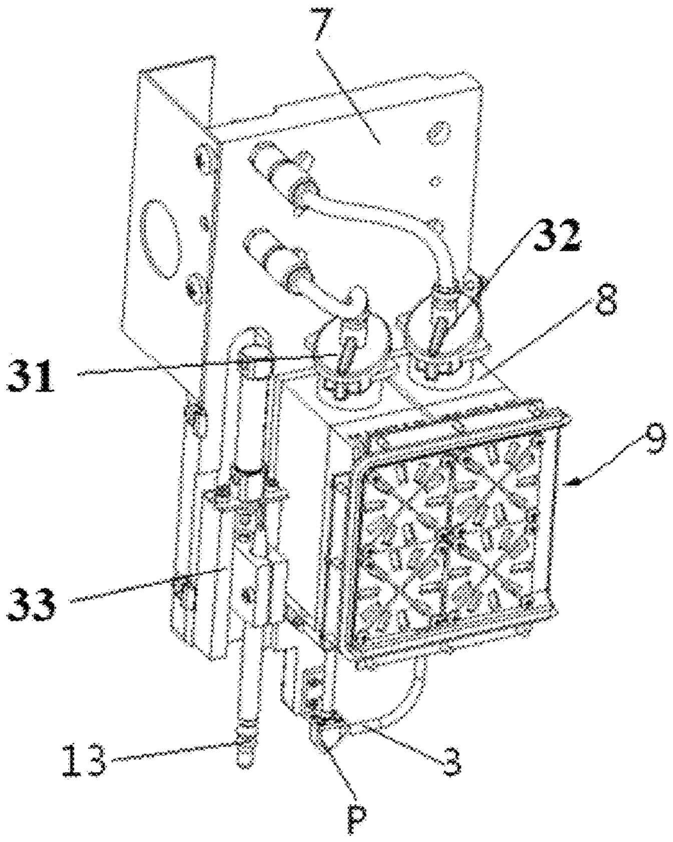
FIG. 4 is a schematic view of the structure of one embodiment of the bioprinter of the present disclosure.
Figure 5:
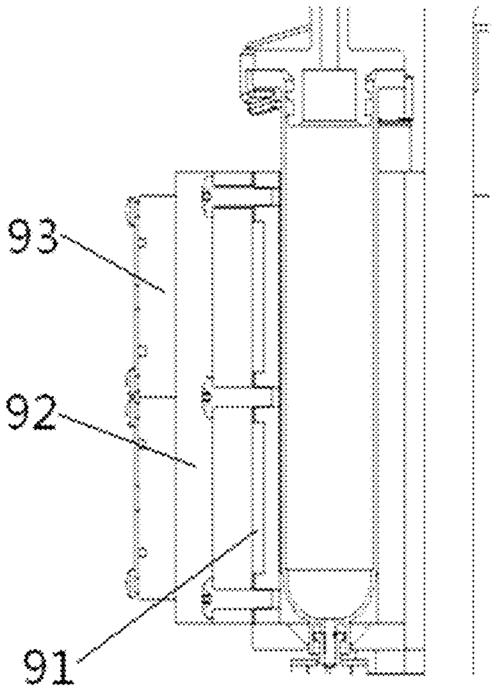
FIG. 5 is a schematic view of the structure of a temperature control device in the bioprinter shown in FIG. 4.

In addition, the present disclosure also provides a bioprinter, in the embodiments shown in FIGS. 4 and 5, which comprises the above-described bioprinter spray head assembly. Since the bioprinter spray head assembly of the present disclosure can wrap the cells during printing so that the cells are protected from damage and present a high survival rate, the bioprinter using such spray head assembly also possesses the corresponding advantageous technical effects, and can enable the produced various biological constructs to maintain a favorable biological property such as a high activity and a long service life by obtaining a high-quality biological printing material. For example, the bioprinter is a 3D bioprinter, and the bioprinter spray head assembly of the present disclosure is especially suitable for a 3D bioprinter.

In one embodiment of the present disclosure, the bioprinter further comprises a fixing plate 7, a mounting support 8, a first material supply vessel 31, and a second material supply vessel 32. The fixing plate 7 serves as a reference of various components in the entire bioprinter. The mounting support 8 is disposed at a position of a middle lower portion at one side of the fixing plate 7. The first material supply vessel 31 and the second material supply vessel 32 are respectively used to accommodate the main material and the auxiliary material, and are arranged side by side latitudinally within the mounting support 8. For example, the material supply vessel may be a container accommodating a material. The nozzle assembly P (see FIG. 4) of the present disclosure is mounted immediately below the first material supply vessel 31 such that the first material supply vessel 31 communicates with the first material channel A, and the second material supply vessel 32 communicates with the second material channel B through the connection tube 3.

For the bioprinter of the embodiment, it is necessary to realize flow of a biological printing material by means of pressure control, for example air pressure control. Thus, the bioprinter may also include a pressure adjustment device, for example selecting an electrical proportional valve etc. The first material supply vessel 31 and the second material supply vessel 32 when filled up with materials are respectively connected with the electrical proportional valve in the air path. The respective corresponding electrical proportional valves of the two material supply vessels are then communicated with the control system in real-time analog amount, and the extrusion amount of the two material supply vessels are respectively controlled via the instructions issued by the upper software. The spraying velocity of the fluid within the first material channel A and the second material channel B may be controlled by respectively adjusting the air pressure.

Different control manners may be adopted according to different printing demands:

When it is necessary to form a continuous biological printing material, first of all, a main material is added within the first material supply vessel 31. The main material is a substance mixture containing cells, whose state may be fluidity and may also be jellylike. An auxiliary material is added within the second material supply vessel 32, and the auxiliary material may be the same substance as the main material (the main and auxiliary materials are of the same material). According to the operational requirements, the auxiliary material may be a nutrient-supplying substance, may also be a substance for providing an adhesive force (which may also be used for forming a protective layer), and may also be substance wrapped around the main material to form a protective layer. Next, by applying a constant air pressure into the first material supply vessel 31 by the pressure adjustment device, the main material may be continuously sprayed, and externally wrapped by the auxiliary material to integrally form an elongated structure.

When it is need to form a granular biological printing material, it is possible to add a main material within the first material supply vessel 31, to add an auxiliary material within the second material supply vessel 32, and to frequently pressurize and open/close the first material supply vessel 31 to generate pulse signals, for controlling that the main material is sprayed from the outlet of the first material channel A in the form of discrete particles; and to apply a continuous pressure into the second material supply vessel 32 for controlling that the auxiliary material is continuously sprayed from the outlet of the second material channel B. Certainly, it is also possible to apply a pulsed pressure into the second material supply vessel 32. With reference to FIG. 3, by pulse signals control of the main material, it is possible to form discrete particles, and combine with the outer layer of auxiliary material to form a fluid printing unit similar to egg, egg yolk covered with egg white, which is rapidly cooled and molded under the effect of temperature.

As a more preferred embodiment, the bioprinter of the present disclosure further comprises a temperature control device 9 for controlling respective temperatures of the main material and the auxiliary material, and the first material supply vessel 31 and the second material supply vessel 32 may use independent temperature control device 9. With reference to FIG. 5, the temperature control device 9 is provided on a side of the mounting support 8 away from the fixing plate 7. The temperature control device 9 sequentially includes from one end proximate to the mounting support 8: a cooling pad 91, a radiator 92, and a radiator fan 93. The cooling pad 91 which is provided near the surface of the mounting support 8 may heat or cool the biological printing material under the control of an external temperature controller. The cooling pad 91 may choose a semiconductor cooling pad, of which a temperature-controlling end is provided opposite to the material supply vessel, and a non-temperature-controlling end is disposed opposite to the radiator 92. The radiator 92 is used for taking away the heat produced by the semiconductor cooling pad during operation, and the radiator fan 93 is used for accelerating the radiation process of the radiator 92. Even further, a temperature detection device may also be provided outside the first material supply vessel 31 and the second material supply vessel 32 to more accurately judge the current temperatures of the main material and the auxiliary material.

In the embodiment, by providing the temperature control device 9, it is beneficial to keep the activity of the biological material in the printing process, and especially when a biological printing material having a high viscosity, it can improve the fluidity and avoid the phenomenon of the clogging of the nozzle due to a low temperature as much as possible, so as to raise the printing efficiency.

In another more preferred embodiment, the bioprinter further comprises a position detection device 13, which is provided in a sliding slot 33 mounted on the fixing plate 7. The position detection device 13 is movable longitudinally along the sliding slot 33, for judging the height of the printing platform before printing to determine an initial printing position of the spray head assembly, thereby printing more accurately.

The above introduces in detail a bioprinter spray head assembly and bioprinter provided by the present disclosure. Specific embodiments are applied in this text to elaborate the principles and embodiments of the present disclosure, and the aforementioned descriptions of the embodiments are only used to help understanding the method of the present disclosure as well as its core thoughts. It should be set forth that, for a person skilled in the art, on the premise of not departing away from the principles of the present disclosure, several modifications and decorations may also be made to the present disclosure, and such modifications and decorations also fall into the protection scope of the claims of the present disclosure.

The invention claimed is:

1. A bioprinter spray head assembly, comprising:

an outer nozzle provided with a second channel, the outer nozzle comprises a first guide portion and a first body portion connected with the first guide portion; and an inner nozzle provided with a first material channel, and the inner nozzle being coaxially provided within the second channel, and the inner nozzle comprises a second guide portion and a second body portion connected with the second guide portion;

wherein an annular space between the outer nozzle and the inner nozzle forms a second material channel, and the second material channel surrounds the first material channel at an outlet of the first material channel to converge a second material sprayed from an outlet of the second material channel toward a first material sprayed from the outlet of the first material channel, so as to form a fluid printing unit;

wherein the first guide portion and the second guide portion are provided adjacent to an outlet of the spray head, and a first annular space between the first guide portion and the second guide portion is tapered along a direction toward the outlet of the second material channel; a second annular space between the first body portion and the second body portion is at least partially tapered towards a direction of the outlet of the second material channel; and an inclination angle of the first guide portion relative to a central longitudinal axis of the outer nozzle is smaller than that of the first body portion relative to the central longitudinal axis of the outer nozzle.

2. The bioprinter spray head assembly according to claim 1, further comprising a first material supply pipe and an outer nozzle fixing portion, wherein the outer nozzle is detachably connected to the outer nozzle fixing portion, and the inner nozzle is detachably connected to the first material supply pipe.

3. The bioprinter spray head assembly according to claim 2, comprising a nozzle kit group consisting of a plurality of nozzles of different specifications, wherein the outer nozzle and the inner nozzle are selected from the nozzle kit group.

4. The bioprinter spray head assembly according to claim 1, wherein at the outlet of the second material channel, an opening of the outer nozzle is lower than that of the inner nozzle.

5. The bioprinter spray head assembly according to claim 1, wherein a portion of the first material channel in the first annular space is elongated, and a portion of the first material channel in the second annular space is at least partially tapered towards a direction of the outlet of the first material channel.

6. A bioprinter, comprising the bioprinter spray head assembly according to claim 1.

7. The bioprinter according to claim 6, further comprising a pressure adjustment device, for controlling respective fluid pressures within the first material channel and the second material channel.

8. The bioprinter according to claim 6, further comprising a temperature control device, for controlling respective temperatures of the first material channel and the second material channel.

9. The bioprinter according to claim 6, further comprising a position detecting device, for judging an initial printing position of the spray head assembly.

* * * * *